United States Patent [19]

Infante

[11] Patent Number: 5,742,064
[45] Date of Patent: Apr. 21, 1998

[54] SYSTEM FOR DETECTING IMPURITIES CONTAINED IN A FLOWING PETROLEUM PRODUCT

[76] Inventor: David A. Infante, 1285 Brooks Rd., Pendergrass, Ga. 30567

[21] Appl. No.: 637,232

[22] Filed: Apr. 24, 1996

[51] Int. Cl.[6] .................. G01N 21/64; G01N 21/85; G01N 21/88
[52] U.S. Cl. .................. 250/458.1; 250/339.12; 250/459.1; 356/70
[58] Field of Search ............ 250/339.07, 339.08, 250/339.11, 339.12, 341.8, 458.1, 459.1, 341.2; 356/70, 337, 442

[56] References Cited

U.S. PATENT DOCUMENTS

| | | |
|---|---|---|
| 4,540,280 | 9/1985 | Anderson et al. |
| 4,588,893 | 5/1986 | Vidrine et al. |
| 5,044,755 | 9/1991 | Landa et al. ............ 356/73.1 X |
| 5,046,854 | 9/1991 | Weller et al. |
| 5,078,493 | 1/1992 | Evens et al. |
| 5,140,169 | 8/1992 | Evens et al. |
| 5,170,056 | 12/1992 | Berard et al. |
| 5,241,368 | 8/1993 | Postingl et al. |
| 5,303,036 | 4/1994 | McLachlan et al. |
| 5,418,614 | 5/1995 | Brost et al. |
| 5,489,536 | 2/1996 | Ekechukwu. |
| 5,495,333 | 2/1996 | Konda et al. |
| 5,557,415 | 9/1996 | Nielsen et al. |

FOREIGN PATENT DOCUMENTS

| | | | |
|---|---|---|---|
| 63-12937 | 1/1988 | Japan .................. | 356/70 |
| 4-20842 | 1/1992 | Japan .................. | 356/337 |
| 1155868 | 5/1985 | U.S.S.R. ............... | 356/70 |
| 1733982 | 5/1992 | U.S.S.R. ............... | 356/70 |
| 2280954 | 2/1995 | United Kingdom ....... | 356/70 |

*Primary Examiner*—Edward J. Glick
*Attorney, Agent, or Firm*—Deveau, Colton & Marquis

[57] ABSTRACT

A method and apparatus for determining the types and amounts of impurities contained in a flowing petroleum product wherein light is projected into the petroleum product, and light which is not absorbed by impurities contained in the petroleum product is transmitted to a spectrometer or photomultiplier. The relationship between the light injected into the petroleum product and the light transmitted out of the petroleum product is analyzed to determine the amounts and types of impurities contained in the petroleum product based on the percentage of light of certain wavelengths transmitted out of the petroleum product. The apparatus comprises a probe which preferably is slip-stream fit to a pipeline through which the petroleum product flows. The probe is coupled to a light source, such as a tunable laser, by a first fiber and to a spectrometer or photomultiplier by a second fiber. Light is transmitted along the first fiber to the probe from the light source and from the probe to a spectrometer or photomultiplier along the second fiber. A third fiber can be coupled to the probe for detecting light fluoresced by impurities contained in the petroleum product so that the types and amounts of impurities contained in the petroleum product can be determined based on characteristics of absorption and/or fluorescence. A plurality of probes may be located along the pipeline at different locations for determining differences between the types and amounts of impurities contained in the petroleum product at different points along the pipeline.

14 Claims, 7 Drawing Sheets

SYSTEM FOR DETECTING IMPURITIES CONTAINED IN A FLOWING PETROLEUM PRODUCT

TECHNICAL FIELD OF THE INVENTION

The present invention relates to a method and apparatus for detecting water and other impurities contained in a fluid medium and, more particularly, to an optical detection system which comprises means for projecting light into a liquid petroleum product flowing through a pipeline, means for detecting the amount of light transmitted through the liquid petroleum product and/or fluoresced by impurities in the liquid petroleum product, and means for determining the amount and/or types of impurities contained in the liquid petroleum product based on the amount of light transmitted and/or fluoresced.

BRIEF SUMMARY OF THE INVENTION

The present invention is particularly well suited for, but is not limited to, detecting impurities contained in petroleum being transported along a pipeline. When oil or petroleum is transported along a pipeline, impurities, such as water and dirt, may enter the pipeline with the petroleum. This type of contamination may occur, for example, when oil or petroleum is introduced into the pipeline from an oil well, ship or tanker. Contamination may also enter the pipeline after the oil or petroleum has been introduced into the pipeline through fractures, faulty seals, and other defects in the pipeline. Water and impurities contained in the petroleum may cause adverse consequences such as, for example, an airplane crash when the airplane cannot properly process the petroleum along with the impurities in the petroleum. The pipeline company may be blamed for injuries attributable to the impure petroleum.

In order to prevent these types of catastrophes from occurring, and to avoid liability, pipeline companies need a method for determining if there are impurities in the petroleum and, if so, whether the impurities were present in the petroleum when it entered the pipelines or whether the presence of the impurities is due to defects in the pipelines. To fulfill this need, the detection system of the present invention was designed for, but is not limited to, detecting water, dirt, diesel fuel and other impurities in petroleum products. The present invention accomplishes these and other objectives by optically detecting and analyzing components contained in the petroleum product to determine the types and/or amounts of impurities contained in the petroleum.

A second purpose of the present invention is to provide an apparatus which optically detects a batch marker substance contained in a petroleum product flowing through a pipeline to determine the presence of a particular "batch" of material flowing through the pipeline. Once the presence of a particular batch has been detected, the batch can be routed to a predetermined destination. In accordance with this embodiment, the wavelength at which the marker substance fluoresces is utilized to determine the presence of the marker substance. Preferably, light absorption characteristics of the marker substance are utilized in addition to the fluorescence characteristics to determine the presence of the marker in the fluid.

In accordance with the present invention, an optical probe having means for projecting and receiving light is disposed in the path of a fluid medium and light is projected by the probe into the fluid medium. Light absorption and/or fluorescence characteristics are then measured and analyzed to determine the amounts and/or types of impurities contained in the fluid.

Accordingly, it is an object of the present invention to provide a method and apparatus for detecting impurities contained in a petroleum product flowing through a pipeline.

It is yet another object of the present invention to provide a method and apparatus for determining whether contaminated petroleum being transported through a pipeline became contaminated prior to the introduction of the petroleum into the pipeline or while the petroleum was being transported through the pipeline.

It is yet another object of the present invention to provide a method and apparatus for detecting impurities contained in a petroleum product by analyzing the wavelength of light reflected (i.e., not absorbed) by the impurities to determine the amounts and/or types of impurities contained in the petroleum product.

It is yet another object of the present invention to provide a method and apparatus for detecting impurities contained in a petroleum product by analyzing the amount of fluorescence fluoresced by the impurities to determine the amounts and/or types of impurities contained in the petroleum product.

It is yet another object of the present invention to provide a method and apparatus which simultaneously measures absorption and fluorescence to determine the types and/or amounts of impurities contained in a petroleum product.

It is yet another object of the present invention to provide a method and apparatus which detects the presence of a batch marker in a petroleum product to control the routing of the petroleum product.

These and other objects of the present invention will become apparent from the following description, drawings and claims.

BRIEF DESCRIPTION OF THE DRAWINGS

FIG. 2b is a front cross-sectional view of a portion of the probe of FIG. 2a; and FIG. 2c is a perspective view of the housing of the probe of FIG. 2a.

DETAILED DESCRIPTION OF THE INVENTION

Figure 1:
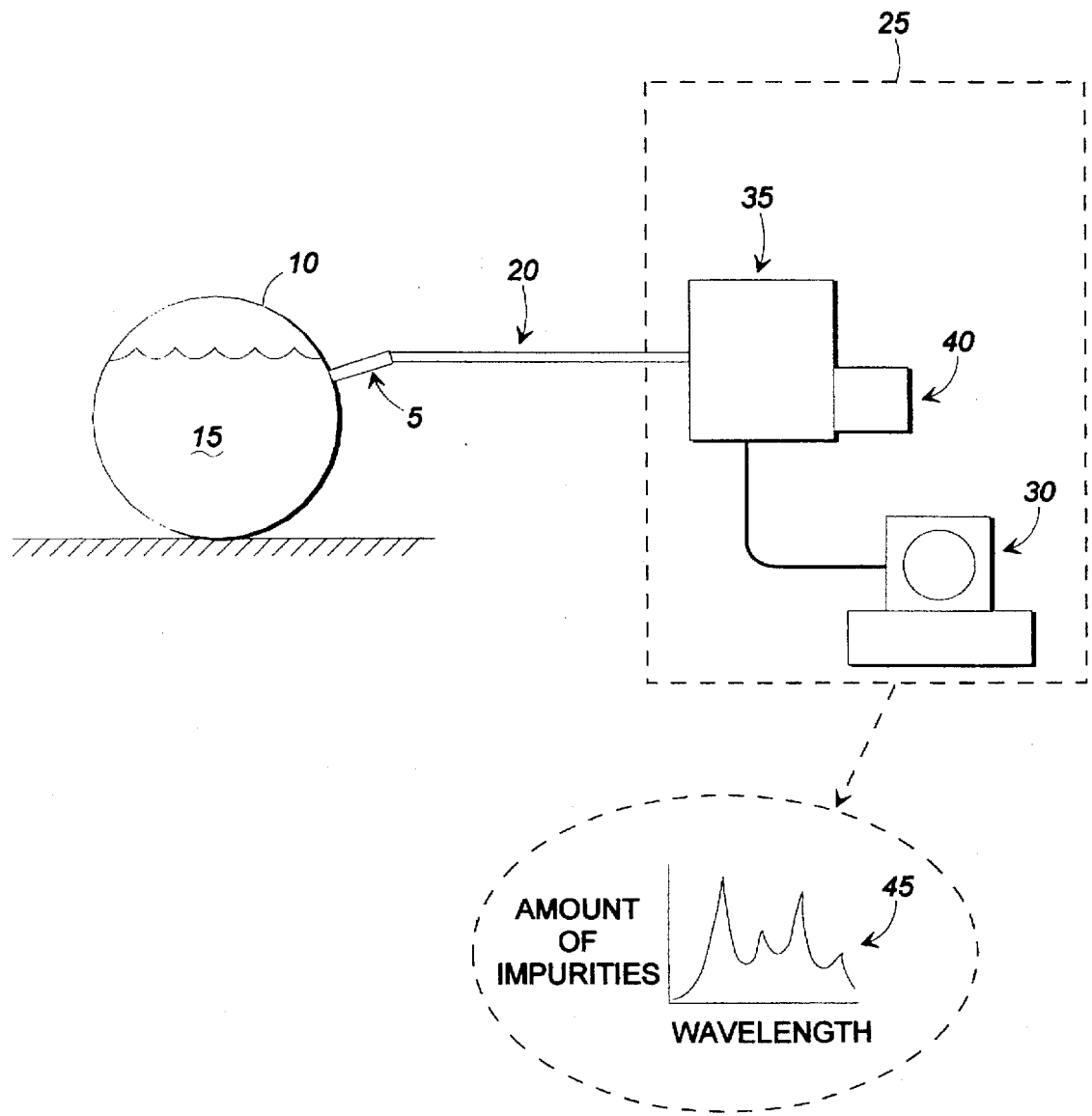
FIG. 1 is a schematic block diagram of the optical detection system of the present invention.

FIG. 1 provides a general illustration of the optical detection system of the present invention in accordance with a first embodiment in which the optical detection system is used to detect water and other impurities contained in petroleum being transported through a pipeline. Probe 5 is preferably connected to the pipe 10 in a slip stream configuration such that fluid 15 from the pipe 10 is routed through probe 5 located outside of pipe 10. An optical waveguide 20 is connected on one end to the probe 5. On the other end of the waveguide 20, opposite probe 5, the waveguide 20 is coupled to an analyzer device 25 which comprises a spectrometer 35 for analyzing the wavelength of light reflected through waveguide 20 to analyzer device 25. A processing means 30, such as a personal computer, is electrically coupled to the spectrometer 35 for receiving data from spectrometer 35 related to the wavelength of light received by spectrometer 35. The processing means 30 is programmed with software which allows it to process the data received from spectrometer 35 to determine the amounts and types of impurities contained in the petroleum, as illustrated by graph 45. Graph 45 represents a typical spectrum plotted by a computer wherein the percentage of light transmitted through the fluid is plotted as a function of wavelength.

In accordance with this first embodiment, the analyzer device 25 comprises a tunable laser 40 for projecting a coherent beam of monochromatic light into a second waveguide (not shown) which is also coupled to probe 5. As light is projected by tunable laser 40 through the waveguide and probe into the petroleum, light is reflected, or back scattered, by the impurities contained within the petroleum into the end of waveguide 20 connected to and disposed inside probe 5, as discussed in detail below with respect to FIGS. 2a–2c. Therefore, the probe 5 is coupled to two waveguides: one for transmitting light from the light source 40 to probe 5 and one for transmitting light from probe 5 to spectrometer 35. The light sensing means, which preferably is simply the end of an optical fiber, causes the reflected light to be propagated along waveguide 20 to the spectrometer 35 which performs the above-mentioned analysis.

In accordance with this first embodiment, two probes are used. A first probe is placed toward the ingress port of the pipeline 10 to quantify the components of the petroleum as they are introduced into the pipeline 10, and a second probe is placed toward the egress port of the pipeline 10 just before the point where the petroleum exits the pipeline for quantifying the components of the petroleum after they have traveled through the pipeline 10. Each of the probes is connected to an analyzer device 25 via a pair of optical waveguides for allowing light to be propagated to and from the analyzer device 25 to and from the pipeline 10.

Figure 2B:
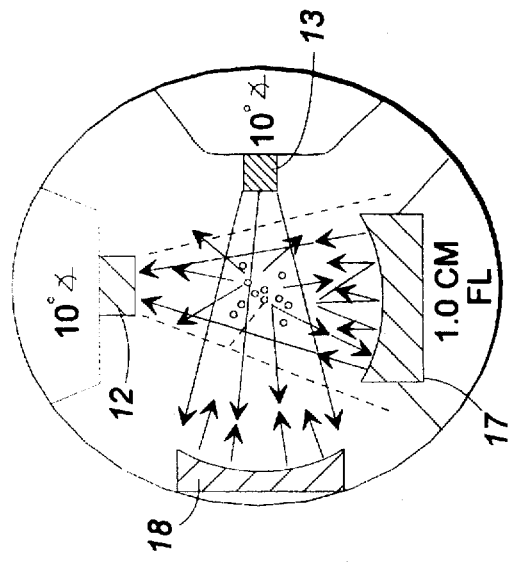
Figure 2C:
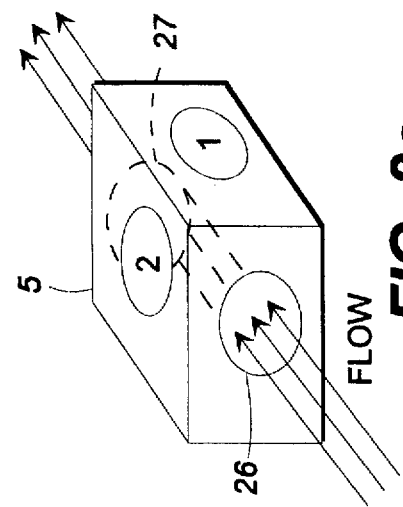
Figure 2A:
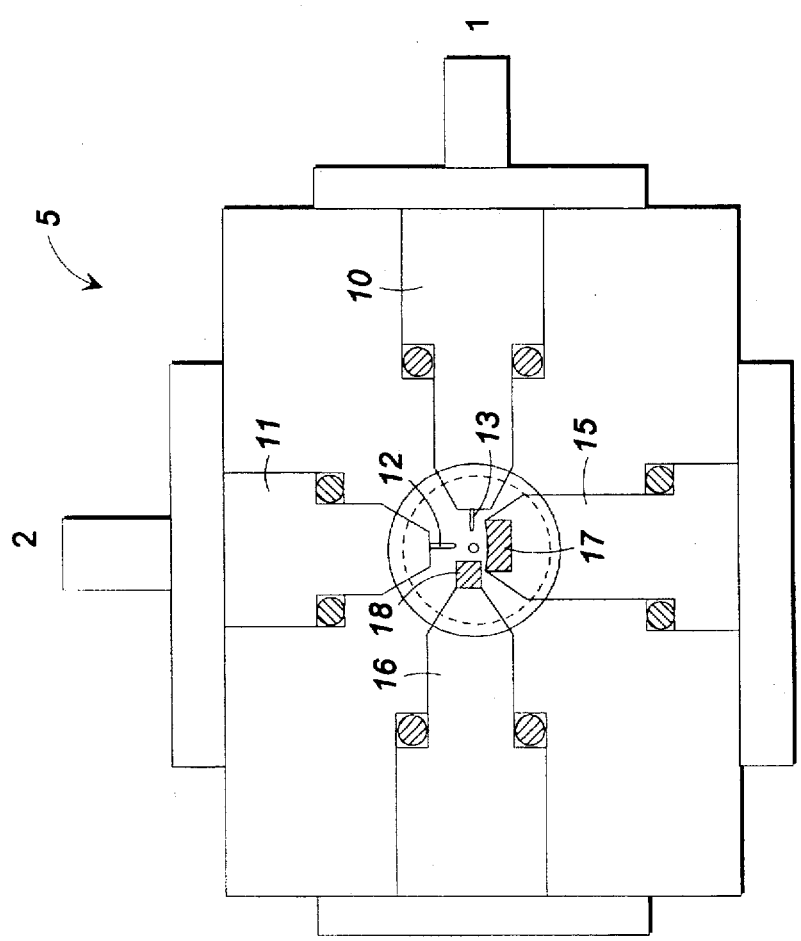
FIG. 2a is a schematic diagram illustrating a front view a first embodiment of the probe of the present invention.

FIGS. 2a–2c schematically illustrate the first embodiment of the probe of the optical detection system of the present invention. FIG. 2a illustrates a front view of the probe. The waveguides are connected to the probe through side and top waveguide openings 1 and 2 and are maintained in their respective positions via mounting means 10 and 11. The waveguide ends 12 and 13 are positioned perpendicular to one another as shown. Mounting means 15 and 16 provide mounting support for concave reflectors 17 and 18, respectively.

In operation, light is projected from the wave source 40 along a first waveguide (not shown) into the probe 5 and through waveguide end 13 into the fluid. Waveguide end 12 receives reflected and back scattered light and transports the light via waveguide 20 to the spectrometer 35 shown in FIG. 1. FIG. 2b is a front cross-sectional view of the portion of the probe in which the waveguide tips 12 and 13 and the reflectors 17 and 18 are positioned in proximity to one another. As light is projected into the fluid passing through the probe, some of the light impinges on concave reflector 18 while some of the light is reflected, or back scattered, by impurities contained in the fluid. Light reflected by the impurities is reflected toward concave reflectors 17 and 18, as well as in other directions, such as toward waveguide tip 12. Light which impinges on concave reflector 18 is reflected back toward the center of the probe. Light reflected by concave reflector 17 is also reflected back toward the center of the probe and toward waveguide tip 12. The positioning of reflectors 17 and 18 results in most of the light being reflected into waveguide tip 12 so that it is propagated back to the analyzer device 25 via waveguide 20.

As shown in FIG. 2c, the probe 5 has one opening 26 for receiving fluid into the probe and a second opening 27 through which the fluid exits the probe. As the fluid flows through the probe 5, light projected into the fluid through waveguide tip 13 impinges on any impurities contained in the fluid and is reflected back to the spectrometer 35 through waveguide tip 12, as described above. The spectrometer 35 is preferably an infrared spectrometer. A fourier transform infrared spectrometer (FTIR) is suitable for this purpose, as is an infrared spectrometer which detects light waves in the near-infrared region. The spectrometer 35 measures the wavelengths of the reflected light and outputs the measurements to computer 30 which compares the measurements obtained to known wavelengths of various substances which are stored in memory to determine the types of impurities contained in the fluid. It will be apparent to those skilled in the art that the computer 30 can be programmed to analyze, correlate and collate the data in any desired manner. A printer (not shown) can be attached to computer 30 so that a printout of the results of the analysis can be obtained.

As stated above, it is preferable that a probe be located at the ingress and egress ends of the pipeline so that the difference between the types and/or amounts of impurities contained in the fluid at the ingress and egress ends can be determined. In accordance with the preferred embodiment, only one probe is located at each end. However, it will be apparent to those skilled in the art that the numbers and locations of the probes which may be used are virtually unlimited. For example, if it were desirable to pinpoint the exact location where impurities are entering a pipeline, probes could be located at set intervals along the pipeline so that changes in the types and/or amounts of impurities contained in the fluid can be measured to determine the point at which the impurities are entering the pipeline. In contrast, if it is only desirable to determine the types and/or amounts of impurities contained in the fluid, and not the difference between the types and/or amounts of impurities at different locations, one probe is sufficient to make that determination. Furthermore, in some cases it may be desirable to insert the probe directly into the pipeline rather than using a slip-stream configuration. In accordance with one embodiment of the present invention, one probe is inserted into the pipeline so that the fluid flows through the probe. Light is projected from the probe into the fluid and the backscattered light is received by the probe and transmitted to the analyzer device which determines the types and amounts of impurities contained in the fluid.

The principles of spectroscopy applied in the present invention are well known. The techniques of spectroscopy most often applied are nuclear magnetic resonance spectroscopy, infrared spectroscopy, and ultraviolet-visible spectroscopy. Infrared spectroscopy and ultraviolet-visible spectroscopy are suitable for use with the present invention. Preferably, infrared spectroscopy is used with the present invention. Therefore, the following discussion of spectroscopy will be directed to infrared spectroscopy.

Infrared radiation corresponds to the portion of the electromagnetic spectrum having wavelengths ranging from approximately 1 to 100 micrometers, or from $10^{-6}$ to $10^{-4}$ meters. When infrared light of a particular wavelength impinges on a molecule, the molecule will absorb the light if the wavelength of the vibrating bond of the molecule is the same as the wavelength of the infrared light. The infrared light which is not absorbed is transmitted and the percentage of infrared light transmitted as well as the wavelengths of the infrared light transmitted can be determined by an infrared spectrometer which plots a strip chart, or spectrum, of the relationship between wavelength (or frequency) and absorption. The spectrum typically is illustrated by a vertical axis which corresponds to percent transmittance of light and a horizontal axis which corresponds to the wavelengths of light transmitted.

A spectrometer typically is comprised of a radiation source which continuously varies the wavelength of the infrared light being generated over the infrared region, a container which holds the sample through which the light passes, and a detector which detects a drop in intensity when the wavelength at which the sample vibrates has been obtained. When the spectrum is plotted, peaks are found at the wavelengths corresponding to the absorption of the light by the sample. These peaks can be used to determine the identity of the sample because generally they are unique for each compound. Since this information is known for many different compounds, the identity of an unknown compound can be determined by superposition of the spectra of known compounds with the spectrum of the unknown compound. In accordance with one embodiment of the present invention, a library of digital representations of spectra for many different compounds is stored in the memory of computer 30 or in some other memory device (not shown) accessible by computer 30. The computer obtains a digital representation of the spectra generated by spectrometer 35 and performs a template matching routine which compares the digital representations stored in memory with the digital representations of the unknown spectrum to determine the types and/or amounts of impurities contained in the fluid.

Figure 3:
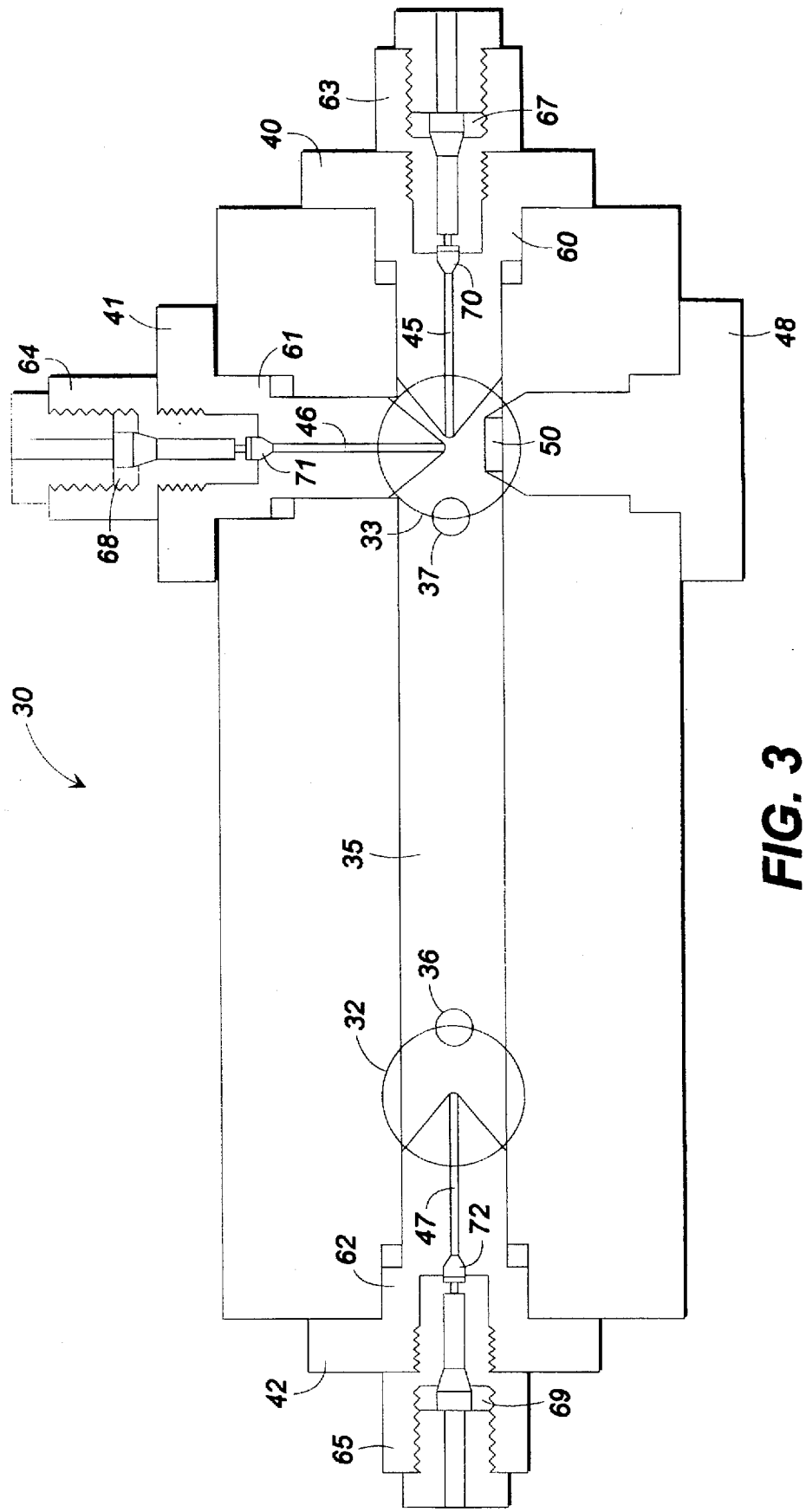
FIG. 3 is a cross-sectional view of a preferred embodiment of the probe of the present invention.

FIG. 3 schematically illustrates a preferred embodiment of the probe of the present invention for measuring impurities contained in a fluid medium. In accordance with this embodiment, absorption and fluorescence are measured simultaneously to determine the types and amounts of certain impurities contained in the fluid medium. The probe 30 is designed to be slip stream fit to a pipeline (not shown). Fluid is routed through probe 30 through openings 32 and 33 which are threaded bores for attaching probe 30 in a slip stream configuration. A longitudinal bore 35 extends through probe 30 from bore 32 to bore 33 to allow fluid to flow into and out of the probe through openings 32 and 33, respectively. Spherical lenses 36 and 37 are mounted within bore 35 adjacent openings 32 and 33 such that fluid flowing through bore 35 washes over lenses 36 and 37. Fiber mounts 40, 41 and 42 are provided for mounting fibers 45, 46 and 47 to the probe 30 such that the ends of the fibers are disposed in openings 32 and 33. An additional mount 48 is attached to the probe 30 opposite fiber mount 41. Mount 48 carries a reflector 50 for reflecting light toward the end of fiber 46. Fiber 45 is used to inject light into probe 30 while fibers 46 and 47 are disposed to receive light, as described in detail below. A light source (not shown) projects light into probe 30 through fiber 45. Analyzing and processing means (not shown) are connected to fibers 46 and 47 for analyzing and processing light received by fibers 46 and 47 to determine the amounts and types of impurities contained in the fluid passing through the probe 30. The analyzing and processing means will be discussed in more detail below with respect to FIG. 4.

In accordance with the preferred embodiment, white light is injected into probe 30 through fiber 45 from a light source such as a tungsten lamp. As the light impinges on impurities contained in the fluid flowing through the probe, the different impurities will fluoresce at particular wavelengths. Fiber 46 detects the fluorescence and transmits the fluorescent light to a filtering circuit and to a photomultiplier which measures the level of fluorescence. Light injected into probe 30 passes through lens 37 into bore 35 and is focused on lens 36. Lens 36 focuses the light into the end of fiber 47. As the light passes through bore 35 and through the fluid, certain wavelengths of light are absorbed while other wavelengths of light are transmitted. The light which is not absorbed is received by fiber 47. The light received by fiber 47 is filtered and certain wavelengths are analyzed to determine the types and amounts of impurities contained in the liquid. Thus, characteristics of fluorescence and absorption are used simultaneously to determine the types and/or amounts of impurities contained in the liquid.

In accordance with the preferred embodiment of the present invention, probe 30 simultaneously detects a batch marker, water, and dirt. For example, when red dye is used as the batch marker, the dye will fluoresce lower wavelengths of blue light. Fiber 46 receives the fluorescent blue light as well as other wavelengths of the source light which are backscattered by the fluid. All wavelengths of light other than the lower wavelengths of blue light are filtered out and the lower wavelengths of blue light are provided to a photomultiplier (not shown). Although the source light also contains some blue light of lower wavelengths, the energy of the fluoresced blue light is much greater than the energy of the source blue light, which allows the source blue light to be disregarded when measuring the fluoresced blue light with the photomultiplier. When the photomultiplier registers a predetermined threshold amount of lower-wavelength blue light, the red dye marker has been detected.

Spherical lens 36 is preferably a 5 mm diameter sapphire lens. As light from the source impinges on lens 37, the light is focused on spherical lens 36, which preferably is a 10 mm sapphire lens. Lens 36 focuses the light into the end of fiber 47 which is coupled to the detection circuitry shown in FIG. 4 and discussed below. The detection circuitry shown in FIG. 4 preferably detects three different bandwidths of light. However, it will be apparent to those skilled in the art that any desired wavelengths of light can be detected and analyzed by utilizing the appropriate optical filters and electrical circuit components. In accordance with the preferred embodiment, the detection circuitry shown in FIG. 4 detects and measures green light, red light and light having a wavelength of 1.94 micrometers.

The detection circuitry in accordance with the preferred embodiment will now be discussed with respect to FIG. 4. The light which passes through the fluid into the end of fiber 47 is split by beam splitter 50 which is a 45° dichroic filter such that only green light is provided to photomultiplier 52. The light reflected from filter 50 is split again by dichroic filter 54 which filters out all wavelengths except red light and the red light is provided to photomultiplier 55. The light reflected from filter 54 is provided to dichroic filter 56 which filters out all wavelengths of light except light having a wavelength of 1.94 micrometers which is provided to photomultiplier 57.

Through experimentation, it was determined that most if not all fluid materials which flow through the pipeline except for dirt or sludge pass red light, and that dirt or sludge attenuates all wavelengths of light substantially uniformly over the region of the electromagnetic spectrum analyzed by the present invention. For this reason it was decided that the attenuation or absorption of red light would be measured and used to calibrate the system of the present invention to determine whether other wavelengths of light detected are being attenuated by dirt or whether they are being absorbed by other types of impurities. Thus, even when dirt is present in the fluid flowing through the pipeline, the types and amounts of other types of impurities can be detected by calibrating the system in accordance with the amount of red light absorbed to compensate for attenuation caused by the dirt.

As stated above, the detection system of the present invention is also suitable for detecting a batch marker. When red dye is used as the batch marker, the dye fluoresces lower-wavelength blue light and absorbs green light. Dichroic filter 58 passes only lower-wavelength blue light to photomultiplier 60 from fiber 46. When a certain threshold level of lower-wavelength blue light is measured by photomultiplier 60 and when the amount of green light measured by photomultiplier 52 is reduced below a certain threshold level, the red dye batch marker is deemed to be present in the fluid. Therefore, absorption and fluorescence characteristics may be utilized simultaneously to determine the presence of the batch marker. When water is present in the fluid, light having the wavelength of 1.94 micrometers is absorbed. Thus, when the amount of light of that wavelength detected and measured by photomultiplier 57 falls below a predetermined threshold, the amount of water present in the fluid is ascertained.

Figure 4:
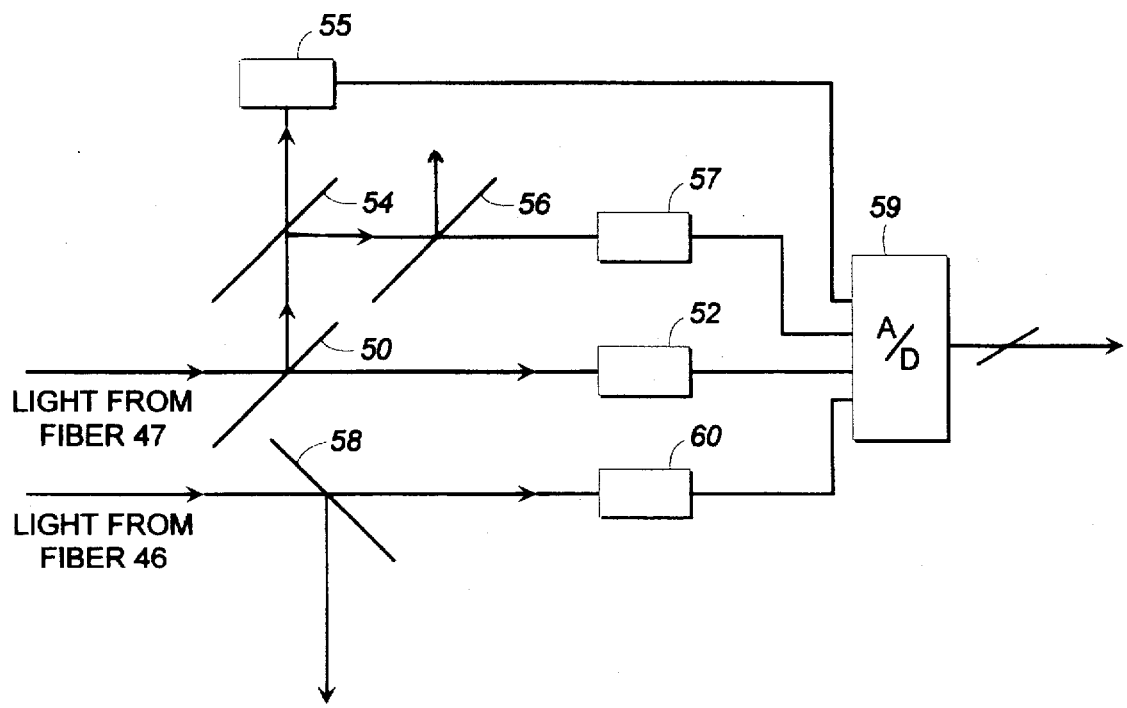
FIG. 4 is a block diagram of the optical detection circuitry of the present invention in accordance with the preferred embodiment.

It will be apparent to those skilled in the art that a spectrometer rather than photomultipliers may be used with the preferred embodiment of FIG. 4 if it is desirable to measure the absorption of many, as opposed to a few, different wavelengths of light. It will also be apparent to those skilled in the art that the simultaneous implementation of fluorescence detection and absorption detection can be used to determine the types and amounts of a variety of different types of impurities contained in the fluid other than those mentioned above. Furthermore, it will be apparent to those skilled in the art that the types and amounts of impurities contained in the fluid, including the batch marker, can be determined using either, rather than both, absorption or fluorescence characteristics.

The information obtained by photomultipliers 52, 55, 57 and 60 is further processed by analog-to-digital converter 59 which converts the analog signals from the photomultipliers into digital information which is output to a processing means such as a personal computer (not shown). The processing means determines whether the batch marker is present in the fluid and the types and amounts of other impurities contained in the fluid based on the information output from the photomultipliers. It will be apparent to those skilled in the art that the processing means can be programmed to process and analyze the information received from analog-to-digital converter 59 in any desired manner.

Referring again to FIG. 3, the probe 30 is preferably comprised of stainless steel 303 and is capable of withstanding pressures of up to 10,000 lbs psi. The spherical lenses 36 and 37 are secured in place by mounting brackets (not shown) such that the fluid flows across the lenses and cleans the lenses. Therefore, the optics of the system in accordance with the preferred design are self-cleaning. The fiber mounts 40, 41 and 42 each have first portions 60, 61 and 62 which are fixedly secured to the probe 30 and second portions 63, 64 and 65, respectively, which are threadedly secured to portions 60, 61 and 62, respectively. Third portions 67, 68 and 69 of the fiber mounts are threadedly secured to second portions 63, 64 and 65 of the fiber mounts. The fibers are secured within the third portions by ferrules 70, 71 and 72 such that the fibers are precisely positioned within the probe 30.

Figure 5:
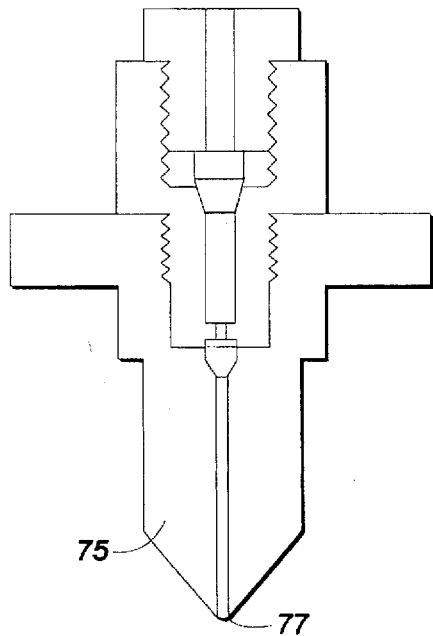
FIG. 5 is a cross-sectional view of one of the optical waveguide mounts of the present invention.

FIG. 5 is a plan view of one of the fiber mounts of probe 30 having a fiber secured therein. The first portion of the fiber mount 75 which is fixedly secured to the probe 30 is cone-shaped and has a small opening 77 formed in the apex thereof. The opening is just large enough to dispose the tip of the fiber adjacent the fluid flowing through the probe 30. Because of the precise manner in which the probe 30 is machined, probe 30 is capable of making the desired measurements while subjected to the extreme pressures characteristic of petroleum pipelines, e.g., 10,000 lbs psi. Nevertheless, it will be apparent to those skilled in the art that the present invention is not limited to the probe designs illustrated in the drawings and that other probe shapes and fiber mount configurations are within the spirit and scope of the present invention.

Figure 6:
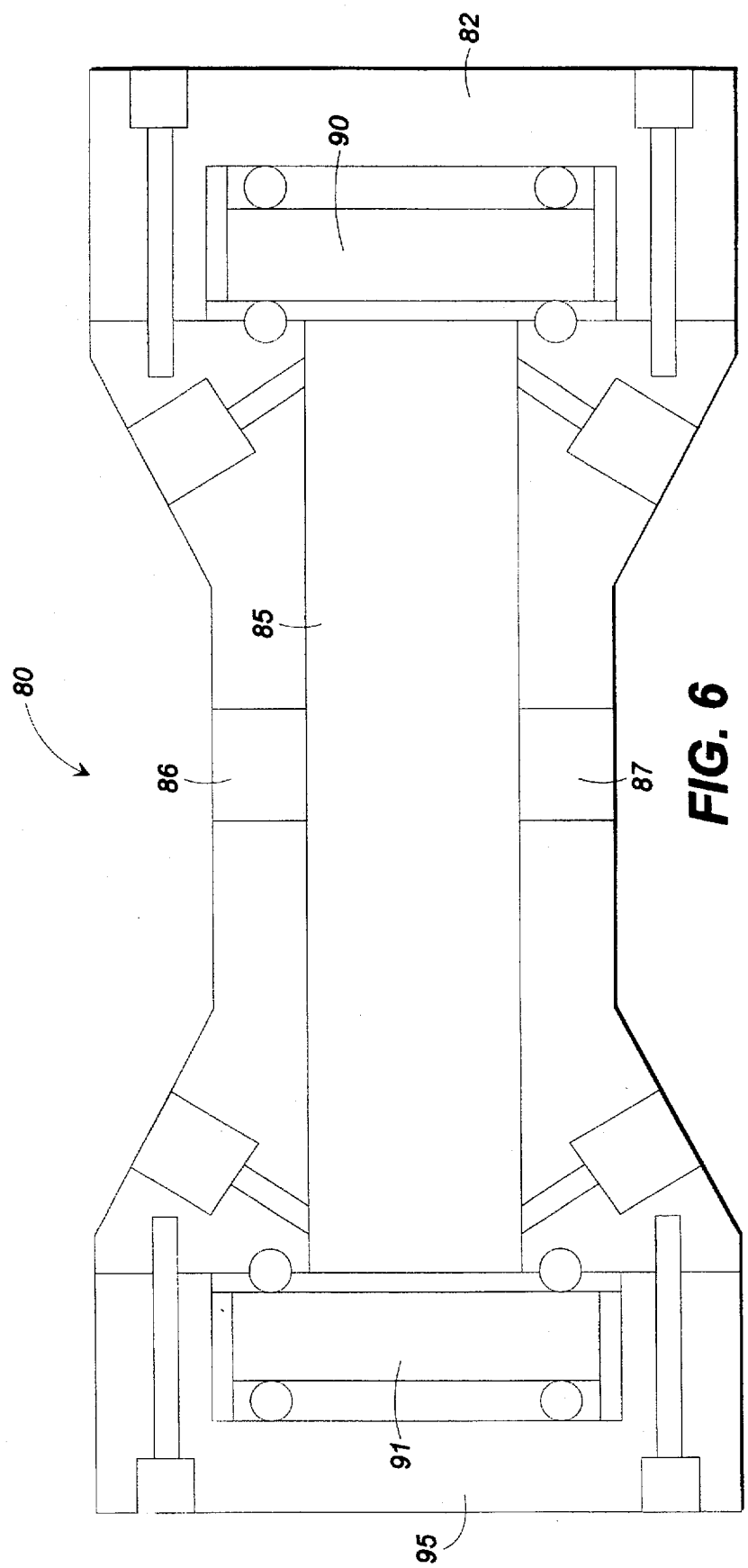
FIG. 6 is a cross-sectional view of an alternative embodiment of the probe of the present invention.

FIG. 6 is an alternative design of the probe of the detection system of the present invention. The probe 80 comprises a first end 82 having an opening formed therein (not shown) through which light from a light source can be projected. A bore 85 extends longitudinally through probe 80 in the axial direction. Openings 86 and 87 are provided in the probe 80 for connecting the probe 80 in a slip stream configuration to a pipeline for allowing fluid to flow into and out of bore 85. Transparent windows 90 and 91 are secured within the probe 80 adjacent the bore 85 for allowing light to be transmitted through the probe 80 from the first end 82 to the second end 95. The second end 95 has an opening formed therein (not shown) through which light exits the probe to a suitable processing means.

Figure 7:
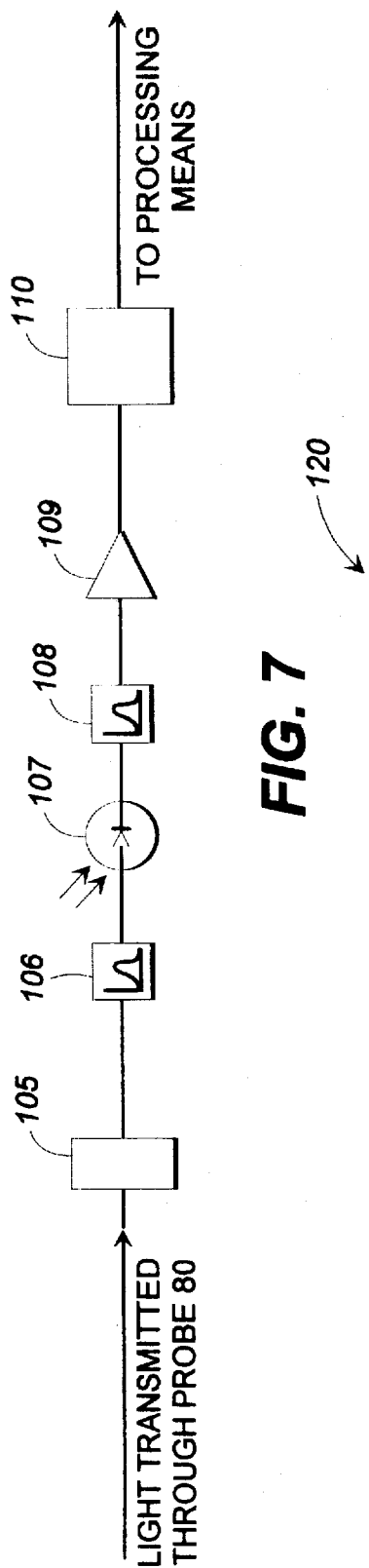
FIG. 7 is a block diagram of the optical detection circuitry of the present invention in accordance with an alternative embodiment.

In operation, optical fibers are secured to ends 82 and 95 through the openings formed therein. Preferably, a 1.94 micrometer wavelength infrared beam is projected through a fiber (not shown) attached at end 82 into the fluid as it flows through the bore 85. A receiving fiber (not shown) attached at end 95 receives light which is not absorbed by the fluid and transmits the light to the processing circuitry illustrated in block diagram form in FIG. 7. As shown in FIG. 7, a 400 Hz chopper 105 chops the received light to compensate for the rise and fall times of photodetector 107 which converts the optical signal into an electrical signal. Filter 106 is an optical filter which passes only a 1.94 micrometer wavelength infrared signal. Filter 108 filters out any noise, removes DC baseline variations and passes a 400 Hz AC signal to amplifier 109. Amplifier 109 amplifies the signal and provides it to an electronic processing display instrument 110, which converts the information into digital for display or further processing by a computer. This information is then transmitted to a processing means (not shown) which determines the parts per million (ppm) of the impurity contained in the fluid. In this particular embodiment, the only impurity being detected is water which absorbs light having a wavelength of 1.94 micrometers. However, it will be apparent to those skilled in the art that this embodiment is not limited to detecting the amount of water contained in the fluid. For example, a white light source can be used in conjunction with appropriate filters and circuit components to determine the amounts and types of a plurality of impurities by using the principals of spectroscopy discussed above. The processing means can be, for example, a spectrometer or a photomultiplier as in the preceding embodiments.

Figure 8:
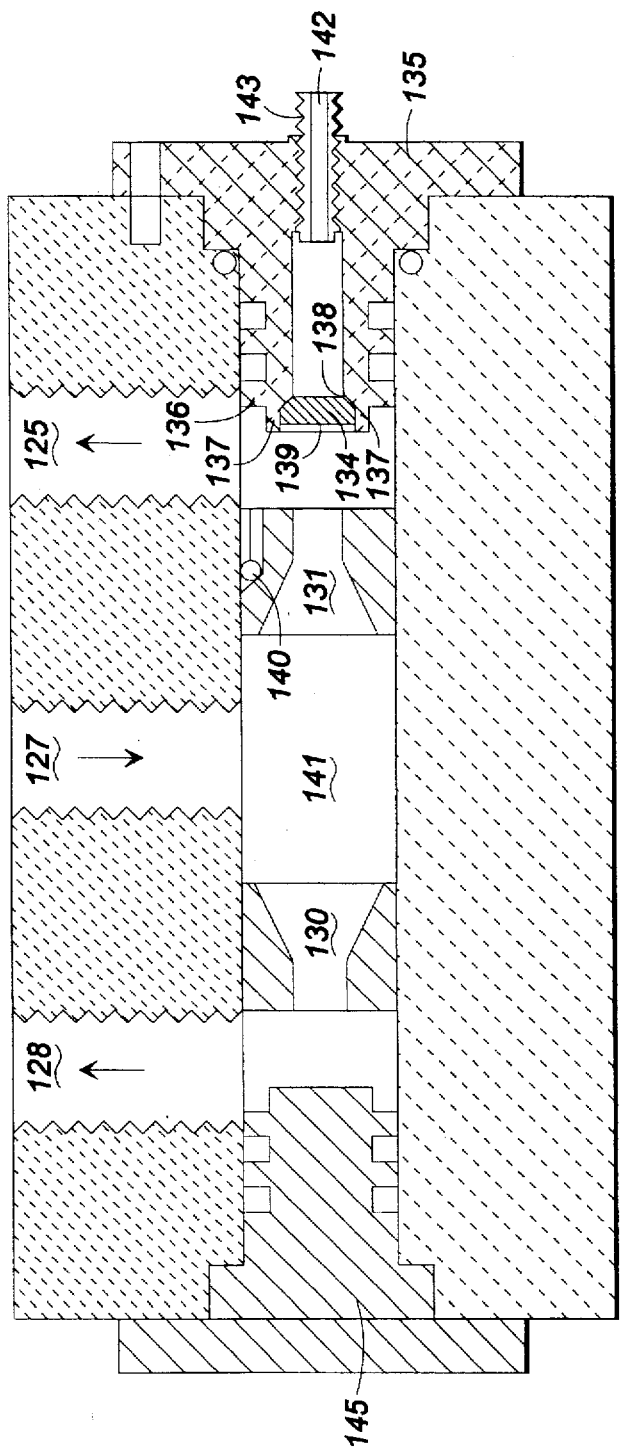
FIG. 8 is a cross-sectional view of an alternative embodiment of the probe of the present invention.

FIG. 8 illustrates a cross-sectional view of an alternative design of the probe of the present invention for detecting and measuring impurities contained in a fluid medium. The probe 120 preferably is attached to a pipeline in a slip-stream configuration such that fluid flows into the probe 120 through threaded bore 127 and out of the probe 120 through threaded bores 125 and 128. As the fluid flows into the probe through bore 127 it enters longitudinal bore 141. The fluid exits longitudinal bore 141 through funnel-shaped ports 130 and 131, which create an increase in fluid pressure as the fluid exits longitudinal bore 141. The funnel-shaped ports 130 and 131 are adjustably positioned within longitudinal bore 141 by means of a ball bearing 140 arranged in a threaded slot as shown which can be adjusted with an Allen wrench.

Each end of probe 120 is provided with an optical coupler which holds an optical fiber and a plano-convex lens. For simplicity, only the right side of the probe 120 is shown in detail in FIG. 8 because the right and left sides of the probe are identical in appearance. A fiber holder 143 holds fiber 142 and is threadedly secured to optical coupler 135 to maintain the end of fiber 142 in a fixed position. A plano-convex lens 134 is held in place by means of an O ring 138 located between lens 134 and fiber 142, and a snap ring 139 interposed between lens 134 and a lip 137 of the optical coupler 135.

As the fluid exits longitudinal bore 141 through funnel-shaped port 131, the increased pressure caused by the shape of port 131 causes the fluid to wash lens 134, and thus the optical system is self cleaning. The optical coupler 135 is provided with radiator fins 136 which allow heat to be transferred to the portions of the lens 134 which are not in contact with the fluid, thereby preventing lens 134 from fogging up.

As the fluid passes through probe 120, light from fiber 142 is focused by lens 134 such that the light impinges on a plano-convex lens (not shown) positioned in the optical coupler located at end 145, which focuses the light into the end of a receiving fiber (not shown). The light transmitted from the end of fiber 138 which is not absorbed as it passes through the fluid is processed by circuitry such as that shown in FIGS. 1, 4 and 7 and discussed above to determine the types and amounts of impurities contained in the fluid by using principles of spectroscopy and/or characteristics of fluorescence.

Figure 9:
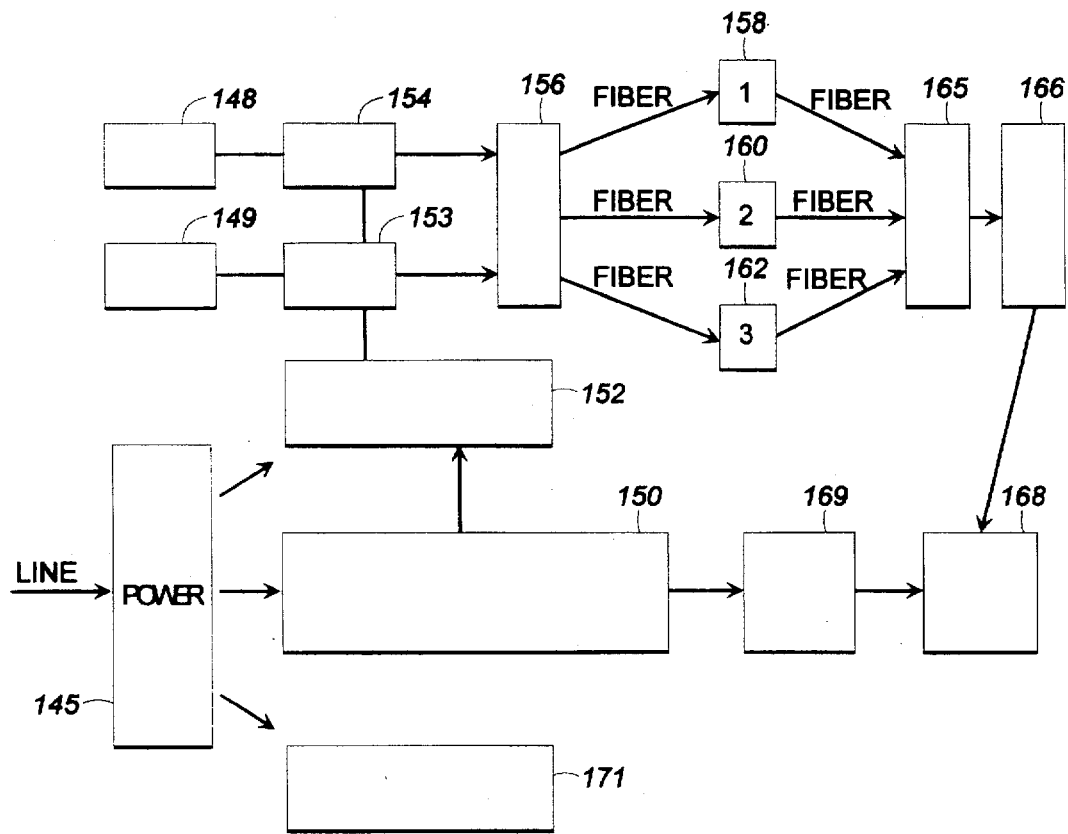
FIG. 9 is a block diagram of the optical detection system of the present invention in accordance with an alternative embodiment.

FIG. 9 is a schematic block diagram of the impurity detection system of the present invention in accordance with an alternative embodiment wherein a plurality of probes are utilized to simultaneously measure impurities in a plurality of pipelines. In accordance with this embodiment, two laser diodes 153 and 154 are used to generate a 670 nm wavelength signal and a 1.94 µm wavelength signal, respectively. The laser diodes are powered by power modules 148 and 149. The laser diodes are fiber coupled to an optical combiner/multiplexer 156 which combines the 1.94 µm and 670 nm signals into a single fiber and provides the combined optical signal to probes 158, 160 and 162. The light which is not absorbed by the fluid flowing through probes 158, 160 and 162 is transmitted to detector circuit 165.

The detector circuit 165 is depicted as a single block for purposes of simplicity. However, in actuality, for each probe there will be a detector circuit which comprises an optical beam splitter, such as that shown in FIG. 4, and two detectors, one for detecting a 1.94 µm signal and one for detecting a 670 nm signal. The signals output from detection circuit 165 are amplified by pre-amp 166 and amplifier 168 prior to being converted into digital by ADC 169. The digital information is provided to computer 150 which determines the amount of absorption of the 1.94 µm and 670 nm wavelength signals in accordance with the principles of spectroscopy discussed above. The results obtained by computer 150 can then be output to, for example, a local area network 171 where the results can be monitored and/or further processed by personnel, or the results can be output to any other desired location.

Power module 145 provides power to the entire system illustrated in FIG. 9. A modulation unit 152 controlled by computer 150 modulates each of the laser diodes 153 and 154 at a rate of 400 Hz to compensate for voltage variations in the output of detector circuit 165 caused by temperature. In essence, laser diodes 153 and 154 are switched on and off at a rate of 400 Hz and ADC 169 samples the amplified output of detector circuit 165 during the intervals when the laser diodes 153 and 154 are on to ensure that voltage variations due to temperature are ignored.

In accordance with the embodiment of FIG. 9, only two types of impurities are detected and measured, namely water and dirt. As discussed in detail above with respect to FIGS. 3 and 4, water absorbs light of 1.94 µm wavelength and dirt absorbs light of 670 nm wavelength. Dirt also uniformly attenuates all other wavelengths of light in the region of the electromagnetic spectrum being analyzed by the present invention. Thus, the amount of light of 670 nm wavelength absorbed by the fluid can be used as a parameter for calibrating the system. Therefore, the system depicted in FIG. 9 measures the amount of water and dirt contained in the fluid in each pipeline and uses the calculation of the amount of dirt in the fluid as a parameter in calculating the amount of water in the fluid.

Figure 10:
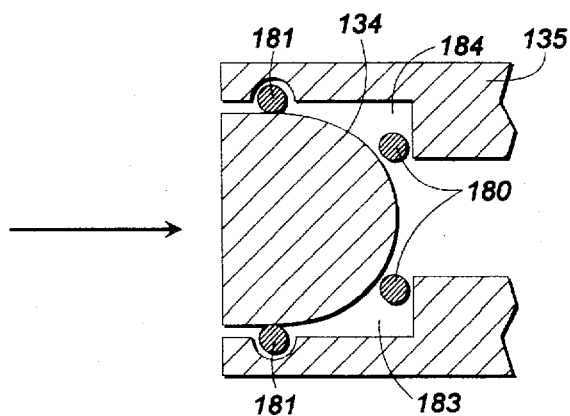
FIG. 10 is a cross-sectional view of a portion of the optical coupler wherein the plano-convex lens is press fit into a double O ring sealing arrangement.

FIG. 10 illustrates an alternative arrangement for securing the plano-convex lens 134 in position within the optical coupler 135 of probe 120. In accordance with this embodiment, plano-convex lens 134 is press fit into the recess in the optical coupler 135 such that one end of lens 134 is pressed against O ring 180 and a portion of lens 134 is circumscribed by O ring 181. Curable epoxy is placed in the areas 183 and 184 of the recess between the O rings 180 and 181. Pressure is then exerted on lens 134 in the direction of the arrow and the epoxy is cured to seal lens 134 in position and prevent it from moving during operation of the system.

It will be apparent to those skilled in the art that variations and modifications can be made to the method and apparatus of the present invention which are within the spirit and scope of the present invention. It will also be apparent to those skilled in the art that the method and apparatus of the present invention is not limited to detecting impurities in petroleum, but that it can be used to detect virtually any substance contained in any fluid medium. It should also be noted that the preferred embodiments discussed above are merely illustrative and that the present invention is not limited to these embodiments. For example, the probes illustrated in FIGS. 2a–2c, 3, 6 and 8 can be constructed in a variety of different ways from a variety of different materials and hardware. Similarly, the detection circuitry can be constructed in a variety of different ways from a variety of different components. It should also be noted that the manner in which the information obtained by the probes is analyzed is not limited to the methods discussed above. It will be apparent to those skilled in the art that software can be written to perform virtually any type of analysis of the information detected by the probe. Furthermore, it will be apparent to those skilled in the art that any of the probes illustrated can be used with any of the impurity detection circuits discussed above.

What is claimed is:

1. A probe for measuring impurities contained in a petroleum product flowing through a pipeline, said probe comprising:

a pressure cell having first and second openings formed therein for allowing the petroleum product to enter and exit the cell, respectively, and a hollow bore extending from the first opening to the second opening for allowing the petroleum product to flow from the first opening to the second opening;

a first optical waveguide mount secured to said cell, said first optical waveguide mount having means for securing a first optical waveguide therein for transmitting light from a light source into the petroleum product flowing through said pressure cell;

a second optical waveguide mount secured to said cell, said second optical waveguide mount having means for securing a second optical waveguide therein for receiving light transmitted by the first optical waveguide through the petroleum product flowing through said cell; and a third optical waveguide mount secured to said cell, said third optical waveguide mount having means for securing a third optical waveguide therein for receiving light fluoresced by impurities contained in the petroleum product flowing through said cell.

2. The device of claim 1 further comprising means for focusing the light transmitted by said first optical waveguide into said second optical waveguide.

3. The device of claim 2 wherein said means for focusing the light comprises a plurality of lenses.

4. The device of claim 1 wherein said first and second optical waveguide mounts are coaxial with said hollow bore and wherein the first and second optical waveguides have ends which face one another such that light transmitted by said first optical waveguide is transmitted from said end of said first optical waveguide toward said end of said second optical waveguide, and wherein the third optical waveguide has an axis which is perpendicular to the axis of the bore and wherein said third optical waveguide has an end disposed adjacent said end of said first optical waveguide.

5. The device of claim 4 wherein at least one lens is mounted within said bore for focusing light transmitted from said first optical waveguide into said end of said second optical waveguide.

6. A method for measuring impurities contained in a petroleum product flowing through a pipeline, said method comprising the steps of:

(1) injecting light into the petroleum product flowing through a pressure cell;

(2) detecting the light injected into the petroleum product which is not absorbed by impurities contained in the petroleum product;

(3) analyzing the light which is not absorbed to determine the types and amounts of impurities contained in the petroleum product;

(4) detecting light fluoresced by impurities contained in the petroleum product; and (5) analyzing the light fluoresced by the impurities to determine the types and amounts of impurities contained in the petroleum product.

7. The method of claim 6 wherein steps (2) and (4) are performed simultaneously within the pressure cell.

8. The method of claim 7 wherein steps (2) and (4) further comprise the steps of filtering out predetermined wavelengths of light.

9. The method of claim 6 wherein steps (3) and (5) are performed simultaneously by a photomultiplier and wherein results obtained from the analysis are used to ascertain the presence or absence of a batch marker contained in the petroleum product.

10. The method of claim 6 wherein results obtained in step (3) are used to determine the presence or absence of water in the petroleum product.

11. The method of claim 10 wherein said results are used to determine the amount of water contained in the petroleum product.

12. The method of claim 6 wherein the results obtained in step (3) are used to determine the amount of dirt contained in the petroleum product.

13. The method of claim 12 wherein the determination of the amount of dirt contained in the petroleum product is utilized in determining the types and amounts of other impurities contained in the petroleum product.

14. The method of claim 6 wherein step (3) is performed by a spectrometer.

* * * * *